(12) United States Patent
Doran-Peterson et al.

(10) Patent No.: US 7,935,503 B2
(45) Date of Patent: May 3, 2011

(54) METHODS FOR PRODUCING AND USING POLYMYXINS

(75) Inventors: Joy Doran-Peterson, Athens, GA (US); Emily Decrescenzo-Henriksen, Idaho Falls, ID (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 12/176,684

(22) Filed: Jul. 21, 2008

(65) Prior Publication Data

US 2009/0081733 A1 Mar. 26, 2009

Related U.S. Application Data

(60) Provisional application No. 60/961,373, filed on Jul. 20, 2007.

(51) Int. Cl.
*C12P 21/04* (2006.01)
(52) U.S. Cl. ...................................... 435/71.3
(58) Field of Classification Search ................... None
See application file for complete search history.

(56) References Cited

U.S. PATENT DOCUMENTS 6,524,827 B2 * 2/2003 Moller et al. .................. 435/74

FOREIGN PATENT DOCUMENTS

WO 01/32835 * 5/2001

OTHER PUBLICATIONS

American Type Culture Collection (ATCCTM) No. 9995TM.*
Henriksen et al (Letters in Applied Microbiology 45:491-496, available on-line Jul. 25, 2007.*
*ATCC Numbers*: American Type Culture Collection, "ATTC No. 6538," organism: *Staphylococcus aureus* subsp. *aureus* Rosenbach; designation: FDA 209 [CIP 4.83, DSM 799, IFO 13276, NCIB 9518, NCTC 10788] [online]; Manassas, VA [retrieved on Mar. 31, 2009] from the Internet. Retrieved from the Internet:<URL: http://www.atcc.org/ATCCAdvancedCatalogSearch/ProductDetails/tabid/452/Default.aspx>; 4 pgs.
*ATCC Numbers*: American Type Culture Collection, "ATTC No. 6633," organism: *Bacillus subtilis* subsp. *spizizenii* Nakamura et al. deposited as *Bacillus subtilis* (Ehrenberg) Cohn; designation: NRS 231 [online]; Manassas, VA [retrieved on Mar. 31, 2009] from the Internet. Retrieved from the Internet:<URL: http://wwvv.atcc.org/ATCCAdvancedCatalogSearch/ProductDetails/tabid/452/Default.aspx>; 4 pgs.
*ATCC Numbers*: American Type Culture Collection, "ATTC No. 9199," organism: *Shigella flexneri* Castellani and Chalmers deposited as *Shigella paradysenteriae* Weldin; designation: AMC 43-G-68 [EVL 82, M134] [online]; Manassas, VA [retrieved on Mar. 31, 2009] from the Internet. Retrieved from the Internet:<URL: http://www.atcc.org/ATCCAdvancedCatalogSearch/ProductDetails/tabid/452/Default.aspx>; 1 pg.
*ATCC Numbers*: American Type Culture Collection, "ATTC No. 11303," organism: *Escherichia coli* (Migula) Castellani and Chalmers; designation: B [CIP 103914, NCIB 11595, NRC 745] [online]; Manassas, VA [retrieved on Mar. 31, 2009] from the Internet. Retrieved from the Internet<URL: http://www.atcc.org/ATCCAdvancedCatalogSearch/ProductDetails/tabid/452/Default.aspx>; 2 pgs.
*ATCC Numbers*: American Type Culture Collection, "ATTC No. 19433," organism: *Enterococcus faecalis* (Andrewes and Horder) Schleifer and Kilpper-Balz deposited as *Streptococcus faecalis* Andrewes and Horder; designation: NCTC 775 [DSM 20478, JCM 8726, NCDO 581, Tissier] [online]; Manassas, VA [retrieved on Mar. 31, 2009] from the Internet. Retrieved from the Internet:<URL: http://www.atcc.org/ATCCAdvancedCatalogSearch/ProductDetails/tabid/452/Default.aspx>; 2 pgs.
*ATCC Numbers*: American Type Culture Collection, "ATTC No. 19615," organism: *Streptococcus pyogenes* Rosenbach; designation: Bruno [CIP 104226] [online]; Manassas, VA [retrieved on Mar. 31, 2009] from the Internet. Retrieved from the Internet:<URL: http://www.atcc.org/ATCCAdvancedCatalogSearch/ProductDetails/tabid/452/Default.aspx>; 2 pgs.
*ATCC Numbers*: American Type Culture Collection, "ATTC No. 27853," organism: *Pseudomonas aeruginosa* (Schroeter) Migula; designation: Boston 41501 [online]; Manassas, VA [retrieved on Mar. 31, 2009] from the Internet. Retrieved from the Internet<URL: http://www.atcc.org/ATCCAdvancedCatalogSearch/ProductDetails/tabid/452/Default.aspx>; 3 pgs.
*ATCC Numbers*: American Type Culture Collection, "ATTC No. 29629," organism: *Salmonella enterica* subsp. *enterica* (ex Kauffmann and Edwards) Le Minor and Popoff serovar Typhimurium deposited as *Salmonella typhimurium* (Loeffler) Castellani and Chalmers; designation: TA 1535 [online]; Manassas, VA [retrieved on Mar. 31, 2009] from the Internet. Retrieved from the Internet<URL: http://www.atcc.org/ATCCAdvancedCatalogSearch/ProductDetails/tabid/452/Default.aspx>; 2 pgs.
*Genbank Accession Number*: National Center for Biotechnology Information, National Library of Medicine, National Institutes of Health, GenBank Locus AY504451, Accession No. AY504451.1, "*Paenibacillaceae bacterium* C25 16S ribosomal RNA gene, partial sequence," [online]. Bethesda, MD [retrieved on Mar. 31, 2009]. Retrieved from the Internet<URL:http://www.ncbi.nlm.nih.gov/nuccore/45331618>; 2 pgs.

(Continued)

*Primary Examiner* — Patricia A Duffy
(74) *Attorney, Agent, or Firm* — Mueting Raasch & Gebhardt, P.A.

(57) ABSTRACT

The present invention provides methods for producing a polymyxin from an isolated *Paenibacillus amylolyticus*, and methods for using the polymyxin, including methods for producing a recombinant polypeptide.

22 Claims, 1 Drawing Sheet

OTHER PUBLICATIONS

*Genbank Accession Number*: National Center for Biotechnology Information, National Library of Medicine, National Institutes of Health, GenBank Locus AY504452, Accession No. AY504452.1, "*Paenibacillaceae bacterium* C26 16S ribosomal RNA gene, partial sequence," [online]. Bethesda, MD [retrieved on Mar. 31, 2009]. Retrieved from the Internet<URL:http://www.ncbi.nlm.nih.gov/nuccore/45331619>; 2 pgs.

*Genbank Accession Number*: National Center for Biotechnology Information, National Library of Medicine, National Institutes of Health, GenBank Locus AY504453, Accession No. AY504453.1, "*Paenibacillaceae bacterium* C27 16S ribosomal RNA gene, partial sequence," [online]. Bethesda, MD [retrieved on Mar. 31, 2009]. Retrieved from the Internet<URL:http://www.ncbi.nlm.nih.gov/nuccore/45331620>; 2 pgs.

*Genbank Accession Number*: National Center for Biotechnology Information, National Library of Medicine, National Institutes of Health, GenBank Locus AY504454, Accession No. AY504454.1, "*Paenibacillaceae bacterium* C28 16S ribosomal RNA gene, partial sequence," [online]. Bethesda, MD [retrieved on Mar. 31, 2009]. Retrieved from the Internet<URL:http://www.ncbi.nlm.nih.gov/nuccore/45331621>; 2 pgs.

*Genbank Accession Number*: National Center for Biotechnology Information, National Library of Medicine, National Institutes of Health, GenBank Locus AY504455, Accession No. AY504455.1, "*Paenibacillaceae bacterium* C29 16S ribosomal RNA gene, partial sequence," [online]. Bethesda, MD [retrieved on Mar. 31, 2009]. Retrieved from the Internet<URL:http://www.ncbi.nlm.nih.gov/nuccore/45331622>; 2 pgs.

*Genbank Accession Number*: National Center for Biotechnology Information, National Library of Medicine, National Institutes of Health, GenBank Locus AY504456, Accession No. AY504456.1, "*Paenibacillaceae bacterium* C30 16S ribosomal RNA gene, partial sequence," [online]. Bethesda, MD [retrieved on Mar. 31, 2009]. Retrieved from the Internet<URL:http://www.ncbi.nlm.nih.gov/nuccore/45331623>; 2 pgs.

Abbott et al., "A method for typing *Shigella sonnei*, using colicine production as a marker," *J. Clin. Pathol.*, Jan. 1958, 11(1):71-77.

Ash et al., "Molecular identification of rRNA group 3 bacilli (Ash, Farrow, Wallbanks and Collins) using a PCR probe test. Proposal for the creation of a new genus *Paenibacillus*," *Antonie Van Leeuwenhoek*, 1993-1994, 64(3-4):253-260.

Atlas, *Handbook of Microbiological Media*, Boca Raton, FL, CRC Press, Inc., 1993, cover page, title page, and table of contents only, 3 pgs.

Berge et al., "*Paenibacillus graminis* sp. *nov.* and *Paenibacillus odorifer* sp. *nov.*, isolated from plant roots, soil and food," *Int. J. Syst. Evol. Microbiol.*, Mar. 2002, 52(Pt 2):607-616.

Claus et al., "Genus *Bacillus*," in *Bergey's Manual of Systematic Bacteriology*, vol. 2, Sneath, ed., Baltimore, MD, The Williams and Wilkins Co., 1986, pp. 1105-1139.

Cook et al., "Isolation of polymer-degrading bacteria and characterization of the hindgut bacterial community from the detritus-feeding larvae of *Tipula abdominalis* (Diptera: Tipulidae)," *Appl. Environ. Microbiol.*, Sep. 2007, 73(17):5683-5686. Available online Jul. 13, 2007.

DeCrescenzo Henriksen et al., "Polymyxin E production by *P. amylolyticus*," *Lett. Appl. Microbiol.*, 2007, 45(5):491-496. Available online Jul. 25, 2007.

Dillon et al., "The gut bacteria of insects: nonpathogenic interactions," *Annu. Rev. Entomol.*, 2004, 49:71-92. Available online as Review in Advance Jul. 23, 2003.

Govaerts et al., "Hyphenation of liquid chromatography to ion trap mass spectrometry to identify minor components in polypeptide antibiotics," *Anal. Bioanal. Chem.*, Nov. 2003, 377(5):909-921. Available online Aug. 30, 2003.

Govaerts et al., "Mass spectrometric fragmentation of cyclic peptides belonging to the polymyxin and colistin antibiotics studied by ion trap and quadrupole/orthogonal-acceleration time-of-flight technology," *Rapid Commun. Mass. Spectrom.*, 2002, 16(9):823-833.

Heyndrickx et al., "A polyphasic reassessment of the genus *Paenibacillus*, reclassification of *Bacillus lautus* (Nakamura 1984) as *Paenibacillus lautus* comb. *nov.* and of *Bacillus peoriae* (Montefusco et al. 1993) as *Paenibacillus peoriae* comb. *nov.*, and emended descriptions of *P. lautus* and of *P. peoriae*," *Int. J. Syst. Bacteriol.*, Oct. 1996, 46(4):988-1003.

Jigami et al., "Identification of a Polymyxin Produced by a Symbiotic Microorganism Isolated from the Brown Planthopper, *Nilaparavata lugens*," *Agric. Biol. Chem.*, Jun. 23, 1986, 50(6), 1637-1639.

Kane et al., "Diversity within diversity: Molecular approaches to studying microbial interactions with insects," *Molecular Ecology and Evolution Approaches and Applications*, Schierwater et al. eds., Switzerland, Birkhauser Verlag Basel, 1994, pp. 509-524.

Kane et al., "Insights from insect-microbe symbioses," in *Biodiversity of Microbial Life*, Staley et al. eds., New York, NY, Wiley-Liss, Inc., 2002, 289-313.

Kenny et al., "Symbiotic micro-organisms of insects: a potential new source for biologically active substances," *Pestic. Sci.*, 1989, 27, 117-131.

Klug et al., "Bacteria Associated with the Gut Tract of Larval Stages of the Aquatic Cranefly *Tipula abdominalis* (Diptera; Tipulidae)," *Appl. Environ. Microbiol.*, Aug. 1980, 40(2), 408-416.

Li et al., "Colistin: the re-emerging antibiotic for multidrug-resistant Gram-negative bacterial infections," *Lancet Infect. Dis.*, Sep. 2006, 6(9):589-601.

Markou et al., "Intravenous colistin in the treatment of sepsis from multiresistant Gram-negative bacilli in critically ill patients," *Crit. Care*, Oct. 2003, 7(5):R78-R83. Available online Jul. 28, 2003.

Martin et al., "Isolation, structural characterization, and properties of mattacin (polymyxin M), a cyclic peptide antibiotic produced by *Paenibacillus kobensis* M," *J. Biol. Chem.*, Apr. 11, 2003, 278(15):13124-13132. Available online Feb. 4, 2003.

Nakamura, "*Bacillus amylolyticus* sp. *nov.*, nom. rev., *Bacillus lautus* sp. *nov.*, norn. rev., *Bacillus pabuli* sp. *nov.*, norn. rev., and *Bacillus validus* sp. *nov.*, norn. rev.," *Int. J. Syst. Bacteriol.*, Apr. 1984, 34(2):224-226.

Reva et al., "Simplified technique for identification of the aerobic spore-forming bacteria by phenotype," *Int. J. Syst. Evol. Microbiol.*, Jul. 2001, 51(Pt 4):1361-1371.

Shida et al, "Emended description of *Paenibacillus amylolyticus* and description of *Paenibacillus illinoisensis* sp. *nov.* and *Paenibacillus chibensis* sp. *nov,*" *Int. J. Syst. Bacteriol.*, Apr. 1997, 47(2):299-306.

Storm et al., "Polymyxin and related peptide antibiotics," *Ann. Rev. Biochem.*, 1977, 46:723-763.

Suzuki et al., "Studies on the Chemical Structure of Colistin. I. Fractionation, Molecular Weight Determination, Amino Acid and Fatty Acid Composition," *J. Biochem.*, 1963, 54:25-33.

Suzuki et al., "The chemical structure of Polymyxin E: The Identities of Polymyxin E1 with Colistin A and of Polymyxin E3 with Colistin B," *J. Biochem.*, Feb. 1965, 57, 226-227.

Theuretzbacher et al., "Nature's clarion call of antibacterial resistance: are we listening?" *Curr. Opin. Investig. Drugs*, Feb. 2006, 7(2):158-166.

DeCrescenzo Henriksen et al., "Lignocellulosic biomass conversion to fuel ethanol: Engineering *Paenibacillus amylolyticus* TA64 for use in enzymatic pretreatment," The University of Georgia Academy for the Environment Symposium: Setting Our Goals High!, Athens, GA, Oct. 23, 2006 Poster; 1 pg., and enlarged version (14 pgs).

Henriksen et al., "Investigationof Lignocellulose Degrading Enzymes from *Paenibacillus amylolyticus* TA64, Isolated from the Hindgut of *Tipula abdominalis*", 2007. ASM 107th General Meeting/ Toronto, Canada. Section No. 048/O, Abstract O-021. 1 page.

Wang et al., "Characterization of a novel thermophilic, cellulose-degrading bacterium *Paenibacillus* sp. Strain B39", 2008. *Letters in Applied Microbology* 47:46-53.

\* cited by examiner

_US 7,935,503 B2_

METHODS FOR PRODUCING AND USING POLYMYXINS

CONTINUING APPLICATION DATA

This application claims the benefit of U.S. Provisional Application Ser. No. 60/961,373, filed Jul. 20, 2007, which is incorporated by reference herein.

BACKGROUND

As bacterial antibiotic resistance continues to increase (Theuretzbacher and Toney, 2006, *Curr. Opin. Investig. Drugs.*, 7, 158-166), habitats rich in microbial diversity merit investigation for novel antimicrobials. Insect-microbe symbioses are ecological niches that harbor diverse microbial consortia, have high levels of species competition, and contain potentially novel organisms. Many species of insects have been shown to harbor diverse gut consortia (Kane and Pierce, 1994, Diversity within diversity: Molecular approaches to studying microbial interactions with insects, IN Schiewater, B. S. B., Wagner, G. P., & Desalle, R. (Eds.) *Molecular Ecology and Evolution Approaches and Applications*. Switzerland, Birkhauser Verlag Basel; Dillon and Dillon, 2004, *Annu Rev Entomol*, 49, 71-92); however, insect-associated microbial consortia have been studied for less than 1% of described insect species (Kane and Mueller, 2002, Insights from insect-microbe symbioses. IN Staley, J. T. & Reysenbach, A.-L. (Eds.) *Biodiversity of Microbial Life*. New York, Wiley-Liss, Inc.). Within a symbiotic environment such as an insect gut, antimicrobials may have dual purpose: associated microorganisms can produce antimicrobials to compete with other microorganisms in the consortia and to prevent colonization by insect pathogens (Dillon and Dillon, 2004, *Annu. Rev. Entomol.*, 49, 71-92).

SUMMARY OF THE INVENTION

The aquatic crane fly, *Tipula abdominalis*, is ubiquitous in stream ecosystems; the larval hindgut hosts a diverse consortia of microorganisms found within the lumen and directly attached to the gut wall (Klug and Kotarski, 1980, *Appl Environ Microbiol*, 40, 408-416). Fifty-nine bacterial isolates have been described (Cook et al., 2007, *Appl Environ Microbiol*, 73:5683-5686) and have been screened for antibacterial production. One group of isolates, with highest 16S rRNA sequence similarity to *Paenibacillus amylolyticus*, secreted antibacterials with broad spectrum activity against both Gram positive and Gram negative bacteria.

The present invention provides methods for producing a polymyxin. The methods may include providing a *Paenibacillus amylolyticus*, preferably an isolated *P. amylolyticus*, incubating the *P. amylolyticus* under conditions suitable for production of polymyxin E1, polymyxin E2, or the combination thereof, and isolating the polymyxin E1, polymyxin E2, or the combination thereof. The *P. amylolyticus* may be obtained from a *Tipula abdominalis* hindgut. The isolating may include preparing a culture supernatant. The method may further include drying the polymyxin E1, polymyxin E2, or the combination thereof, by spray drying, freeze drying, tunnel drying, vacuum drying, or air drying, for instance.

The methods may include providing a *Paenibacillus amylolyticus*, preferably an isolated *P. amylolyticus*, incubating the *P. amylolyticus* under conditions suitable for production of polymyxin E1, polymyxin E2, or the combination thereof, and drying the *P. amylolyticus* and the polymyxin E1, polymyxin E2, or the combination thereof. The *P. amylolyticus* may be obtained from a *Tipula abdominalis* hindgut. The drying may be done by spray drying, freeze drying, tunnel drying, vacuum drying, or air drying, for instance.

The present invention also provides methods for producing a recombinant polypeptide. The methods may include incubating a eukaryotic cell with *Paenibacillus amylolyticus* under conditions suitable for growth of the eukaryotic cell and production of polymyxin E1, polymyxin E2, or the combination thereof by the *P. amylolyticus*, wherein the eukaryotic cell produces a recombinant polypeptide. The eukaryotic cell may be a yeast cell. The method may further include isolating the recombinant polypeptide.

The methods may include incubating a eukaryotic cell with polymyxin E1, polymyxin E2, or a combination thereof, under conditions suitable for growth of the eukaryotic cell, wherein the eukaryotic cell produces a recombinant polypeptide, and wherein the polymyxin E1, polymyxin E2, or combination thereof is produced by incubating *P. amylolyticus* under conditions suitable for production of polymyxin E1, polymyxin E2, or the combination thereof. The eukaryotic cell may be a yeast cell. The method may further include isolating the recombinant polypeptide. The eukaryotic cell may be incubated with the *P. amylolyticus*.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

The term "and/or" means one or all of the listed elements or a combination of any two or more of the listed elements.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention.

The present invention is illustrated by the following examples. It is to be understood that the particular examples, materials, amounts, and procedures are to be interpreted broadly in accordance with the scope and spirit of the invention as set forth herein.

DETAILED DESCRIPTION OF ILLUSTRATIVE EMBODIMENTS

Figure 1:
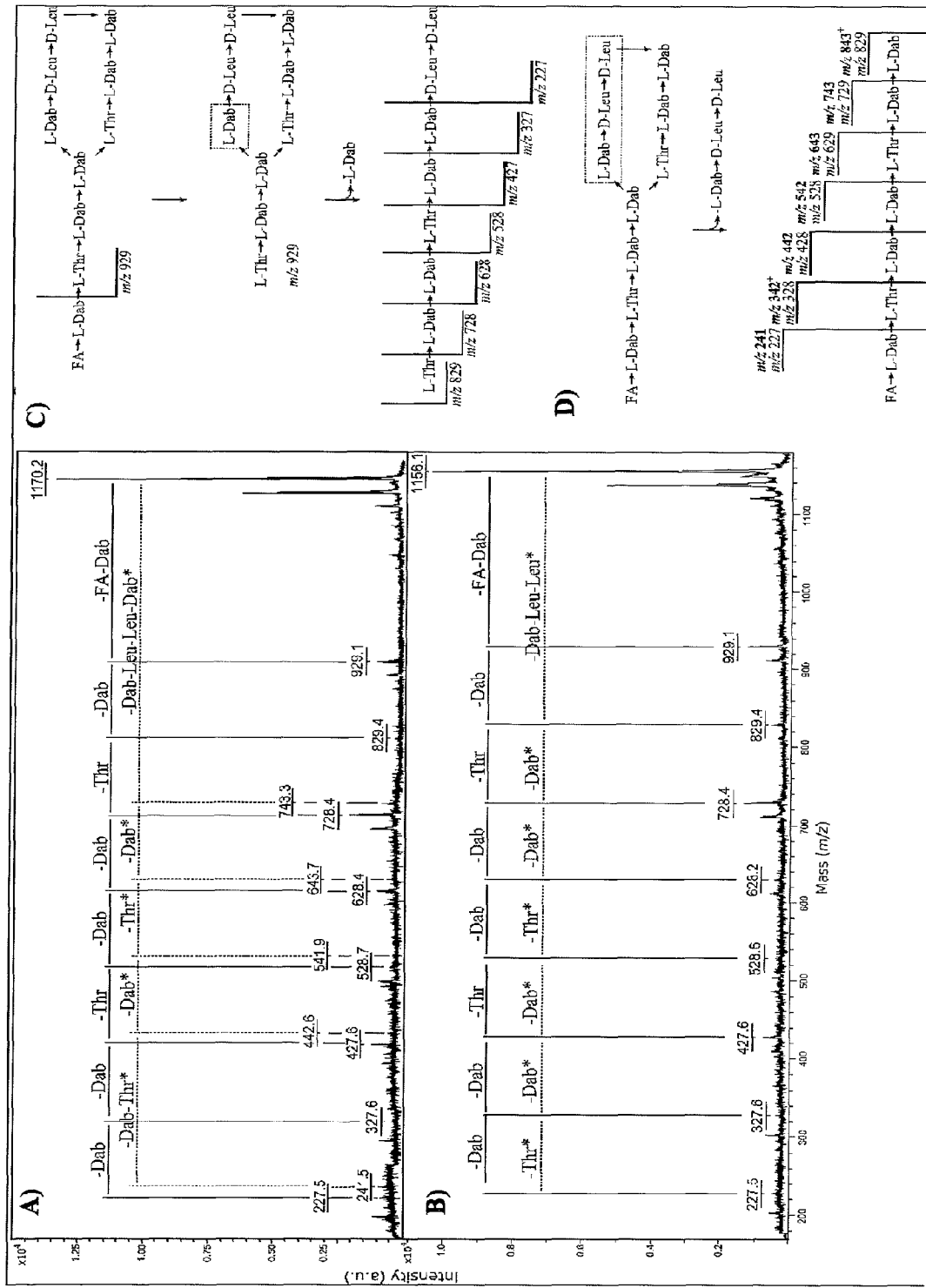
FIGS. 1. A and B. Post-source decay of *P. amylolyticus* C27 antimicrobials. For the antimicrobial $R_t$=38 minutes (1170 m/z [MH$^+$]) (A) the first fragmentation series is denoted by solid lines and begins when the terminal fatty acid moiety (6-methyloctanoyl) and Dab are lost, resulting in m/z 929.8 ion; fragmentation then continues sequentially. The second series, denoted by dotted lines, begins with fragmentation on the cyclic peptide portion of the molecule with loss of Dab-Leu-Leu-Dab, followed by sequential fragmentation. For the antimicrobial $R_t$=33 minutes (1156 m/z [MH$^+$]) (B), the first and second fragmentation series, which are denoted by solid and dotted lines, respectively, are difficult to distinguish as the expected m/z ions for both series in within one m/z; therefore, the m/z ions obtained in the PSD spectra can correlate to species in both the first and second series. Fragmentation occurs in the same manner as the first antimicrobial. An asterisk denotes m/z ions of the second series. C and D, Proposed mechanism of MALDI fragmentation for polymyxin $E_1$ and $E_2$. C shows the primary route of fragmentation for the first series, as observed by PSD spectra (A and B), and D shows the primary route of fragmentation for the second series, as observed by PSD (A and B), with m/z values in bold and plain font for polymyxin $E_1$ and $E_2$, respectively. +Fragments were not observed in PSD experiments.

The present invention includes methods for making a polymyxin. The methods typically include providing a *Paenibacillus amylolyticus*, and incubating the *P. amylolyticus* under conditions suitable for production of a polymyxin. The incubation conditions are typically aerobic. The medium may be liquid or solid, preferably liquid, and may be either minimal or complete, preferably a minimal medium, such as Davis minimal media. The incubation temperature can vary from 25° C. to 37° C., and is preferably 28° C. Conditions that are "suitable" for an event to occur, such as production of a polymyxin, or "suitable" conditions are conditions that do not prevent such events from occurring. Thus, these conditions permit, enhance, facilitate, and/or are conducive to the event.

A polymyxin produced by a *P. amylolyticus* is preferably polymyxin E1 (also known as colistin A) or polymyxin E2 (also known as colistin B). A *P. amylolyticus* may produce both. A polymyxin produced by a *P. amylolyticus* typically includes leucine and threonine, and either lysine, 2,4-diaminobutyric acid, or a combination thereof. The molecular weight of a polymyxin produced by a *P. amylolyticus* is typically 1,155 or 1,169 Daltons. The polymyxyins are cyclical polypeptides having the structure shown in FIG. 1C, where the fatty acid moiety (FA) is 6-methyloctanoic acid or 6-methylheptanoic acid.

Whether a microbe is a *P. amylolyticus* can be determined by routine methods (Cook et al., 2007, *Appl. Environ. Microbiol.*, 73:5683-5686). A *P. amylolyticus* may be obtained from the hindgut of the insect *Tipula abdominalis*. The production of a polymyxin by a *P. amylolyticus* (whether obtained from the hindgut of *T. abdominalis* or from another source) can be determined by routine screening methods. For instance, a candidate *P. amylolyticus* can be incubated under conditions suitable for replication, preferably aerobic conditions, and other microbial isolates (referred to as indicator strains) can be exposed to the candidate *P. amylolyticus*. A candidate *P. amylolyticus* is the isolate being assayed for the production of a polymyxin. Indicator strains may be either Gram negative (such as, but not limited to, *E. coli* and *Salmonella* spp.) or Gram positive (such as, but not limited to, *Staphylococcus aureus* and *Bacillus subtilis*). Preferably, a polymyxin produced by a *P. amylolyticus* inhibits growth of both Gram negative and Gram positive indicator strains, but is more effective against Gram negative indicator strains. Methods for using indicator strains to evaluate the activity of a polymyxin are routine and known to the skilled person. For instance, the indicator strains can be exposed to a culture supernatant obtained from medium in which the candidate *P. amylolyticus* was grown, or the indicator strains can be grown on the same solid medium as the candidate *P. amylolyticus* in such a way to result in overlapping growth of the candidate *P. amylolyticus* and the indicator strains. The inhibition of growth of an indicator strain is evidence the *P. amylolyticus* produces a polymyxin.

The methods of the present invention may further include isolating, and, preferably, purifying a polymyxin produced by *P. amylolyticus*. An "isolated" polymyxin is one that is separate and discrete from its natural environment. For instance, a polymyxin that is present in a culture supernatant from which *P. amylolyticus* cells have been removed is "isolated." Another example includes isolating a polymyxin by drying the mixture of cells and culture supernatant, or drying the culture supernatant. Preferably, the culture or culture supernatant is further treated to sterilize it. For example, the culture can be treated by exposure to conditions to kill the *P. amylolyticus* present in the culture. Examples of conditions useful for sterilization include heat or ultraviolet radiation. The culture may be dried until essentially all moisture is removed and a powder containing the polymyxin remains. Methods for drying cultures are known in the art and include, for instance, spray drying, freeze drying, tunnel drying, vacuum drying, and air drying. The result of such methods is a sterile mixture that includes a large number of components, including the polymyxin. A "purified" polymyxin is one that is at least 80% free, preferably 90% free, and most preferably 95% free from other components with which they are naturally associated. Methods for isolating and purifying the polymyxins described herein are known in the art and routine.

The present invention is also directed to methods of using the polymyxins described herein. The methods include, for instance, pharmaceutical applications, personal care applications, and recombinant polypeptide production. The methods may include preventing microbial growth by a bacteriostatic activity or a bacteriocidal activity of the polymyxin.

Pharmaceutical and personal care applications include, for instance, methods of treating an animal to inhibit, preferably prevent microbial growth. As used herein, "treatment" and "treating" refer to the use of a polymyxin to prevent, cure, retard, or reduce the severity of signs in a subject resulting from the presence of a microbe, and/or result in no worsening of signs over a specified period of time in an subject which has already been exposed to a microbe that can cause the signs. Treatment may be prophylactic or, alternatively, may be initiated after the exposure of an animal to a microbe. Prophylactic treatment refers to the use of a polymyxin to inhibit, preferably prevent microbial growth, thereby preventing or reducing signs of a condition if the subject is later exposed to a microbe. As used herein, the term "signs" refers to objective evidence in a subject of a condition caused by the presence of a microbe. Signs can vary depending upon the microbe. Signs of conditions caused by the presence of a microbe and the evaluation of such signs are routine and known in the art. Accordingly, the present invention is also directed to methods for treating a microbial infection in an animal, and methods for treating a condition caused by a microbe. As used herein, a "microbial infection" refers to a detrimental colonization of an animal by a microbe.

The methods include administering an effective amount of a polymyxin to an animal having an infection and/or signs of a condition caused by a microbe, and determining whether the infection and/or signs of the condition have decreased.

The methods may include administering a polymyxin to an animal. The animal may be any animal susceptible to a condition caused by a microbe including, but not limited to, a vertebrate, more preferably a mammal. Examples of mammals include, but are not limited to, a human; a member of the subfamily Bovinae, such as cattle and bison; a member of the subfamily Caprinae, such as sheep and goats; a member of the genus *Sus*, such as pigs and hogs; companion animals, such as cats and dogs; and a member of the genus *Equus*, such as horses and donkeys. Another example of a vertebrate is a fish. A polymyxin may be delivered to an animal by methods described herein and known in the art, thereby providing an effective amount to the animal. In this aspect of the invention, an "effective amount" is an amount effective to inhibit growth of a microbe, prevent the manifestation of signs of the condition, decrease the severity of the signs of the condition, and/or complete remove the signs. It is not required that a polymyxin completely inhibit growth of all microbes, or completely cure or eliminate all signs of a condition being treated.

A polymyxin described herein may be present in a composition. For instance, a composition may include a pharmaceutically acceptable carrier. As used herein "pharmaceutically acceptable carrier" may include saline, solvents, dispersion media, coatings, antibacterial and antifungal agents, isotonic and absorption delaying agents, and the like, compatible with pharmaceutical administration and not deleterious to a recipient thereof. The polymyxin present in the composition may be isolated or purified. An isolated compound may be one that is isolated by drying the cells or culture supernatant. Additional active compounds can also be incorporated into the compositions.

A composition for administration to a subject may be prepared by methods known in the art of pharmacy. In general, a composition can be formulated in a dosage form to be compatible with its intended route of administration. Examples of routes of administration include, but are not limited to, perfusion; parenteral, e.g., intravenous, intradermal, intramuscular, subcutaneous; topical, e.g., mucosal (such as nasal, sublingual, vaginal, buccal, or rectal) and transdermal; otic; and oral. Solutions or suspensions can include the following components: a sterile diluent such as water for administration, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; buffers such as acetates, citrates or phosphates; electrolytes, such as sodium ion, chloride ion, potassium ion, calcium ion, and magnesium ion, and agents for the adjustment of tonicity such as sodium chloride or dextrose. pH can be adjusted with acids or bases, such as hydrochloric acid or sodium hydroxide. A composition can be enclosed in ampoules, disposable syringes or multiple dose vials made of glass or plastic.

Compositions can include sterile aqueous solutions (where water soluble) or dispersions and sterile powders for the extemporaneous preparation of sterile solutions or dispersions. For intravenous administration, suitable carriers include physiological saline, bacteriostatic water, or phosphate buffered saline (PBS). A composition is typically sterile and, when suitable for injectable use, should be fluid to the extent that easy syringability exists. It should be stable under the conditions of manufacture and storage and optionally preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various optional antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the active compound (i.e., a polymyxin) in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

For topical administration compositions of the invention may include various mixtures and combinations that can be applied topically and to permit even spreading and absorption into cutaneous and mucosal surfaces. Examples include sprays, mists, aerosols, lotions, creams, aqueous and non-aqueous solutions or liquids, oils, gels, powders, ointments, pastes, unguents, emulsions and suspensions. Topical formulations may be prepared by combining a compound of the present invention with conventional pharmaceutical or cosmeceutical diluents or carriers commonly used in topical dry, liquid, cream and aerosol formulations. Both liquids and powders can be delivered as sprays, mists or aerosols.

The active compounds may be prepared with carriers that will protect the active compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. The materials can also be obtained commercially. Liposomal suspensions can also be used as pharmaceutically acceptable carriers. These can be prepared according to methods known to those skilled in the art.

The data obtained from cell culture assays and animal studies can be used in formulating a range of dosage for use in animals, including humans. The dosage of the polymyxins lies preferably within a range of circulating concentrations that include the $ED_{50}$ with little or no toxicity. The dosage may vary within this range depending upon the dosage form employed and the route of administration utilized. For a compound used in the methods of the invention, the therapeutically effective dose can be estimated initially from cell culture assays. A dose may be formulated in animal models to achieve a concentration range that includes the $IC_{50}$ (i.e., the concentration of the test compound which achieves a half-maximal inhibition of signs) as determined in cell culture. Such information can be used to more accurately determine useful doses.

In those aspects where a composition is being administered to an animal for a pharmaceutical application or a personal care application, the composition can be administered one or more times per day to one or more times per week, including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a animal can include a single treatment or, preferably, can include a series of treatments.

The present invention includes both patient-specific dosages forms, as well as non-patient-specific multi-dosage forms that can be used to decontaminate populations exposed to pathogens as a consequence of a bioterrorism attack.

The present invention also includes methods for using polymyxins in the incubation of a eukaryotic cell. Such methods are useful to prevent growth of prokaryotic microbes when incubating eukaryotic cells, especially during fermentations such as those used for the production of recombinant polypeptides for therapeutic, diagnostic, and industrial applications. In one aspect, the methods may include incubating eukaryotic cells with P. amylolyticus under conditions suitable for growth of the eukaryotic cells and production of a polymyxin by the P. amylolyticus. In another aspect, the methods may include adding a polymyxin to a culture of eukaryotic cells. The eukaryotic cells may be yeast cells (such as, but not limited to, Pichia pastoris, Arxula adeninivorans, Candida boidinii, Hansenula polymorpha, Kluyveromyces lactis, Yarrowia lipolytica, or Saccharomyces cerevisiae) or mammalian cells (such as, but not limited to, human cells). Preferably, the eukaryotic cell includes a coding region encoding a recombinant polypeptide. Eukaryotic cells are routinely used for the production of various types of recombinant polypeptides, and the present invention is not limited to the recombinant polypeptide expressed by the cell. Examples of recombinant polypeptides include, for instance, cytokines (including various hematopoietic factors and interleukins) interferons, growth factors, hormones, protease inhibitors, and antibiotics. In some aspects, methods of the present invention do not include incubation of a eukaryotic cell for fermentation of lignocellulose.

The desired products produced by eukaryotic cells may be further isolated, and optionally purified, from the eukaryotic cells using protocols, methods and techniques that are known in the art. For instance, once polypeptides have been separated from cell debris, the recombinant polypeptide can be further purified using purification methods that are known in the art. Suitable protein purification procedures can include fractionation on immunoaffinity or ion-exchange columns; ethanol precipitation; reverse phase HPLC; chromatography on silica or on an ion-exchange resin such as DEAE; chromatofocusing; SDS-PAGE; ammonium sulfate precipitation; gel filtration using, for example, Sephadex G-75; and ligand affinity chromatography.

EXAMPLES

Experimental Procedures

Bacterial Strains and Culture Conditions. *Paenibacillus amylolyticus* C27, C25, C26, C28, and C30 were isolated from the hindgut extract of a *Tipula abdominalis* larva as described in Cook et al. (2007, *Appl. Environ. Microbiol.*, 73:5683-5686), and grown aerobically at 28° C. on tryptic soy agar (TSA) and in tryptic soy both (TSB) or Davis minimal media broth (MM) (Atlas, 1993, *Handbook of Microbiological Media*, Boca Raton, Fla., CRC Press, Inc.). *Escherichia coli* ATCC 11303 was grown aerobically at 37° C. on Luria-Bertani agar or in broth. *Enterococcus faecalis* ATCC 19433, *Pseudomonas aeruginosa* ATCC 27853, *Salmonella typhimurium* ATCC 29629, *Shigella fexneri* ATCC 9199, *Bacillus subtilis* ATCC 6633, *Staphylococcus aureus* ATCC 6538, and *Streptococcus pyogenes* ATCC 19615 were grown aerobically at 37° C. on TSA.

Antibacterial Screening. Antibacterial production was assessed via the cross-streak method (Abbott and Shannon, 1958, *J Clin Pathol*, 11, 71-77) with the primary streak of a *T. abdominalis* bacterial isolate on TSA for 24-48 hours incubation at 28° C. Secondary streaks were incubated for 48 hours at 28° C. Test organisms included: *E. coli* ATCC 11303, *S. aureus* ATCC 6538, and *B. subtilis* ATCC 6633.

Identification of *P. amylolyticus* C27. 16S rRNA gene sequencing and analysis was performed by Midi Labs, Inc. (Newark, N.J.) and sequence data have been submitted to GenBank databases under accession numbers AY504451-6, for isolates C25, C26, C27, C28, and C30, respectively. Biochemical assays were performed with C27 to confirm identification using standard laboratory procedures (Table 1) (Shida et al, 1997, *Int J Syst Bacteriol*, 47,299-306, Reva et al., 2001, *Int J Syst Evol Microbiol*, 51, 1361-1371, Kerr and McHale, 2003, *Applications in General Microbiology*. Winston-Salem, N.C., Hunter Textbooks, Inc.).

TABLE 1

Phenotypic characteristics of P. amylolyticus C27 and closely related organisms.

| Characteristic | 1 | 2 | 3 | 4 | 5 | 6 |
|---|---|---|---|---|---|---|
| Anaerobic growth | + | + | + | + | + | + |
| Catalase | + | + | + | + | + | − |
| Oxidase | − | − | − | − | − | − |
| Nitrate reduction | + | + | − | − | v | − |
| Acid from: | | | | | | |
| Arabinose | + | + | + | + | + | − |
| Glucose | + | + | + | + | + | + |
| Mannitol | + | + | + | + | + | − |
| Xylose | + | + | + | + | + | − |
| Gas from carbohydrates | − | − | − | − | + | − |
| Production of: | | | | | | |
| Acetylmethylcarbinol | − | − | − | − | + | − |
| Indole | − | − | − | − | − | − |
| Hydrolysis of: | | | | | | |
| Caesin | w | w | v | w | + | − |
| Starch | + | + | + | − | + | − |
| Use of citrate | − | − | − | − | − | − |
| Growth in: | | | | | | |
| 2% NaCl | + | + | + | + | + | − |
| 5% NaCl | − | − | − | − | − | NT |
| 0.001% lysozyme | + | − | − | v | v | + |
| Growth at: | | | | | | |
| 50° C. | − | − | − | + | − | − |
| pH 5.6 | + | + | + | + | + | − |

Species: 1, P. amylolyticus C27; 2, P. amylolyticus (Nakamura, 1984, Int J Syst Bacteriol, 34: 224-226; Shida et al, 1997, Int J Syst Bacteriol, 47, 299-306); 3, P. pabuli (Heyndrickx et al., 1996, Int J Syst Bacteriol, 46: 988-1003; Nakamura, 1984, Int J Syst Bacteriol, 34: 224-226; Shida et al, 1997, Int J Syst Bacteriol, 47, 299-306); 4, P. illinoisenis (Berge et al., 2002, Int J Syst Evol Microbiol, 52: 607-616; Shida et al, 1997, Int J Syst Bacteriol, 47, 299-306); 5, P. polymyxa (Claus and Berkeley, 1986, Bacillus. IN Sneath, ed., Bergey's Manual of Systematic Bacteriology. Baltimore, The Willimas and Wilkins Co.; Heyndrickx et al., 1996, Int J Syst Bacterial, 46: 988-1003); 6, P. popilliae (Claus and Berkeley, 1986, Bacillus. IN Sneath, ed., Bergey's Manual of Systematic Bacteriology. Baltimore, The Willimas and Wilkins Co.).v, variable, 10-89% of strains positive; w, weak; NT, not tested.

Assay for Antibacterial Activity. Antibacterial activity of the *Paenibacillus* isolates was assessed qualitatively by spread plating *E. coli* onto TSA and adding up to 50 µL of culture supernatant or antibiotic with incubation at 37° C. for 12 to 16 hours. A zone of inhibition was interpreted as a positive result.

Purification of Antibacterial. *P. amylolyticus* C27 was grown aerobically on TSA at 28° C. for 16 hours, and a 50 mL preculture of MM was inoculated at 28° C. with shaking (250 rpm) for 16 hours. Ten mL of preculture was used to inoculate 500 mL of MM at 28° C. with stirring for 96 hours. Cells were removed by centrifugation (10000×g, 25 min) and filtration (Millipore ExpressPlus 0.22 µm vacuum filter). Purification of the antimicrobial was similar to that described for Polymyxin M (Martin et al., 2003, *J Biol Chem*, 278, 13124-13132). Following isopropanol elution off an Amberlite XAD-16 column, two steps of reverse phase HPLC were performed using a $C_{18}$ column (Supelco, 0.46×25 cm, 5 µm). All identifiable peaks were assayed for activity to determine elution time. A 16% to 50% v/v isopropanol in water (0.1% v/v TFA) gradient over 45 minutes at a flow rate of 0.5 mL $min^{-1}$ was followed by a 50% to 90% v/v methanol in water (0.1% v/v TFA) gradient over 50 min at a flow rate of 0.5 mL $min^{-1}$. The antibacterials eluted at $R_1=33$ and 38 min, as a small broad peak and sharp peak, respectively. Using this method, approximately 3 mg of combined antimicrobials were purified per L of culture.

Minimum inhibitory concentrations. Both *P. amylolyticus* C27 peaks with antibacterial activity from HPLC purification of 500 mL minimal media culture were combined. For analysis of polymyxin B (Sigma-Aldrich, St. Louis, Mo.), polymyxin E (Sigma-Aldrich, St. Louis, Mo.), and the *P. amylolyticus* C27 antibacterials, MIC determinations were performed according to the National Committee for Clinical Laboratory Standards (NCCLS) (Table 2) (NCCLS, 2003, Methods for dilution antimicrobial susceptibility tests for bacteria that grow aerobically; approved standard—sixth edition. NCCLS document M7-A6. Wayne, Pa., National Committee for Clinical Laboratory Standards). MIC analysis was performed in triplicate and results did not vary.

ride was added and the solution was extracted with chloroform. The chloroform layer was partitioned with water, anhydrous sodium sulphate was added to remove trace water, and the chloroform layer was dried. Sample was dissolved 1:1 in methanol:water and mixed with sinapinnic acid for MALDI analysis to detect the fatty acid methyl ester.

Results

Antibacterial activity screening and identification of *P. amylolyticus* C27. Fifty-nine isolates from the hindgut of *T. abdominalis* were screened for antibacterial activity using the cross-streak method (Abbott and Shannon, 1958, *J Clin Pathol*, 11, 71-77). Five isolates inhibited growth of both *E. coli* and *S. aureus*. Partial 16S rDNA sequencing and Blast homology searches in the NCBI nucleotide database revealed the antibacterial producing organisms had 99.1% identity to *Paenibacillus amylolyticus*, which is a Gram positive, spore-forming, facultative anaerobe (Ash et al., 1993, *Antonie Van Leeuwenhoek*, 64, 253-260, Shida et al, 1997, *Int J Syst Bacteriol*, 47, 299-306); this organism has been isolated from four *T. abdominalis* insects in different states from both the hindgut lumen and wall. One strain, designated C27, was chosen for further analyses and biochemical tests were performed to confirm the species identity with comparison to

TABLE 2

Minimum inhibitory concentrations for Polymyxins B and E and the *P. amylolyticus* C27 antimicrobials. MICs were performed in triplicate, and identical values were obtained each time.

| Test Organisms | Polymyxin B (mg L$^{-1}$) | Polymyxin E (mg L$^{-1}$) | *P. amylolyticus* C27 (mg L$^{-1}$) |
|---|---|---|---|
| Gram Positive | | | |
| *Enterococcus faecalis* ATCC 19433 | >128 | >128 | >128 |
| *Staphylococcus aureus* ATCC 6538 | 32 | 128 | 128 |
| *Streptococcus pyogenes* ATCC 19615 | 32 | >128 | >128 |
| Gram Negative | | | |
| *Escherichia coli* ATCC 11303 | 2 | 2 | 2 |
| *Pseudomonas aeruginosa* ATCC 27853 | 4 | 4 | 4 |
| *Salmonella typhimurium* ATCC 29629 | 4 | 1 | 1 |
| *Salmonella typhimurium* ATCC 29629 | 4 | 2 | 2 |

Amino acid analysis. The major active peak ($R_t=38$ min) was evaporated and resuspended in $dH_2O$ at a concentration of 1 mg mL$^{-1}$. Ten µL was run on a Beckman amino acid analyzer at the W.M. Keck Foundation Biotechnology Resource Laboratory at Yale University. Ten nmol L$^{-1}$ diaminobutyric acid was used as a standard.

Mass Spectrometric Analysis. Matrix-assisted laser desorption/ionization (MALDI) and Post Source Decay (PSD) analysis was performed on both *P. amylolyticus* C27 peaks ($R_t=33$ and 38 min) from HPLC purification as well as polymyxin E (Sigma) and MM culture supernatant for the remaining five *Paenibacillus amylolyticus* isolates. The matrix used for MALDI analysis was a saturated solution of alpha-cyano-4-hydroxy cinnamic acid in 1:1:0.01 ratio of acetonitrile:water:trifluoroacetic acid. Sample was mixed with matrix solution in a 1:1 ratio on the target plate and allowed to dry at room temperature. A Bruker Daltonics Inc, Autoflex was used to acquire MALDI and PSD spectra. Ions of interest for PSD analysis were selected using a ±10 m/z isolation window.

Fatty Acid Analysis. A mixed sample of both *P. amylolyticus* antimicrobials was lysed and methylated using 1 mol l$^{-1}$ methanolic-HCl at 80° C. for 18 hours, cooled on an ice bath, and flushed with dry nitrogen. Half-saturated sodium-chloother *Paenibacillus* species (Table 1) (Shida et al, 1997, *Int J Syst Bacteriol*, 47, 299-306, Reva et al., 2001, *Int J Syst Evol Microbiol*, 51, 1361-1371).

Assay for Antibacterial Activity. Antibacterial screens from *P. amylolyticus* C27 whole culture supernatant revealed activity against Gram negative species; cross-streak screenings with live cells exhibited inhibition of *S. aureus*. From minimal media, two compounds with an identical spectrum of antibacterial activity against Gram negative bacteria were isolated. MIC assays were performed on purified antimicrobials and the spectrum of activity for the *P. amylolyticus* compounds was identical to polymyxin E and similar to polymyxin B (Table 2). All three compounds had low MIC values against the Gram negative organisms tested. MIC values were higher for Gram positive organisms, with polymyxin B more effective than both polymyxin E and *P. amylolyticus* C27 antibacterials.

Structure Determination. Initial MALDI analysis of the two active peaks from the final HPLC purification, $R_t=33$ and 38 min, revealed molecular weights of 1155 and 1169 Daltons, respectively. Amino acid analysis revealed the peptides are composed of leucine (Leu), threonine (Thr), with lysine and/or 2,4-diaminobutyric acid (Dab), which co-elute. Based upon the molecular weight, amino acid composition, and spectrum of activity, the compounds were suspected to be polymyxin $E_1$ and $E_2$ (1169 and 1155 Daltons, respectively) (Suzuki et al., 1965, *J Biochem,* 57, 226-227, Suzuki et al., 1963, *J Biochem,* 54, 25-33). To confirm the antibacterials' identifications, Post source decay (PSD) mass spectrometry was employed on m/z 1170 ($MH^+$) and 1156 ($MH^+$) ions for both commercial polymyxin E and the *P. amylolyticus* antibacterials (FIGS. 1, A and B); identical fragmentation patterns were obtained. And, while only accurate to one m/z, fragmentation patterns are similar to those obtained by previous mass spectrometric studies (Govaerts et al., 2003, *Anal Bioanal Chem,* 377, 909-921, Govaerts et al., 2002, *Rapid Commun Mass Spectrom,* 16).

To confirm the fatty acid moiety of the *P. amylolyticus* compounds, fatty acid methyl esters were examined using MALDI-TOF ion scanning. Using this method, the 6-methyloctanoic acid of the more abundant polymyxin $E_1$ was detected.

Screening of *P. amyolyticus* isolates for polymyxin E production. *P. amylolyticus* isolates C25, C26, C28, and C30 were examined for production of polymyxins $E_1$ and $E_2$ using MALDI analysis and qualitative antibacterial assays. Presence of a peak at 1170 ($MH^+$) and/or 1156 ($MH^+$) m/z in the MALDI spectrum and antibacterial activity identical to polymyxin E indicated the presence of the antimicrobial(s). All of the isolates were positive for the production of both polymyxin $E_1$ and $E_2$.

Discussion

Many species within the genus *Paenibacillis* produce variants of the peptide antimicrobial polymyxin, whose general structure consists of a decapeptide with a terminal fatty acid moiety (Storm et al., 1977, *Ann Rev Biochem,* 46, 723-763, Martin et al., 2003, *J Biol Chem,* 278, 13124-13132). Polymyxins differ in amino acid and fatty acid composition and are formed by condensation reactions in the cytoplasm, directed by peptide synthases (Marahiel et al., 1997, *Chem Rev,* 97, 2651-2673). Although toxicity limited its medical applications during the past 50 years, the emergence of drug-resistant pathogens has caused a resurgence of clinical use (Markou et al., 2003, *Critical Care,* 7, R78-R83, Li et al., 2006, *Lancet Infect Dis,* 6, 589).

*P. amylolyticus* isolate C27 produces polymyxins $E_1$ and $E_2$ (colistin A and B), representing a novel source for production of these antimicrobials (Suzuki et al., 1965, *J Biochem,* 57, 226-227, Suzuki et al., 1963, *J Biochem,* 54, 25-33) as well as the first description of antibiotic production for this *Paenibacillus* species. Using a three-step purification protocol, polymyxin $E_1$ and $E_2$ were separated and identified through comparison to commercial polymyxin E (composed of polymyxins $E_1$ and $E_2$). Fragmentation patterns observed for the compounds were nearly identical to previous studies, within the mass accuracy of PSD (Govaerts et al., 2003, *Anal Bioanal Chem,* 377, 909-921, Govaerts et al., 2002, *Rapid Commun Mass Spectrom,* 16). In FIGS. 1C and 1D, a proposed mechanism of fragmentation for polymyxin E is outlined, but others are possible.

Although fatty acid methyl ester (FAME) analysis only detected 6-methyloctanoic acid from *P. amylolyticus* polymyxin $E_1$, the PSD spectra for both polymyxin $E_1$ and $E_2$ exhibit fragments characteristic of their respective fatty acid moieties. MICs were identical for commercial and *P. amylolyticus* antibiotics, although assays with live cells suggest *P. amylolyticus* C27 may produce other antibacterial compounds with activity against Gram positive bacteria.

Bacterial symbionts of insects that produce polymyxin antibiotics in culture have been isolated previously. A yeast isolated from eggs of the brown planthopper *Nilaparvata lugens* was found to produce polymyxin $M_1$ (Jigami et al., 1986, *Agric. Biol. Chem.,* 50, 1637-1639), and a *Bacillus polymyxa* strain isolated from the oriental stinkbug *Plautia stali* produced polymyxin $E_1$ (Kenny et al., 1989, *Pestic. Sci.,* 27, 117-131). However, this is the first investigation of antibacterial production by microorganisms isolated from the hindgut of *Tipula abdominalis*. While production of the antibiotic has not been demonstrated in situ, polymyxin E could have a role in colonization resistance and species competition as established in other insect species.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for producing a polymyxin comprising:
   providing a *Paenibacillus amylolyticus*;
   incubating the *P. amylolyticus* under conditions suitable for production of polymyxin E1, polymyxin E2, or the combination thereof;
   isolating the polymyxin E1, polymyxin E2, or the combination thereof; and
   evaluating the activity of the polymyxin E1, polymyxin E2, or the combination thereof.

2. The method of claim 1 wherein the isolating comprises preparing a culture supernatant.

3. The method of claim 1 further comprising drying the polymyxin E1, polymyxin E2, or the combination thereof.

4. The method of claim 1 further comprising purifying the polymyxin E1, polymyxin E2, or the combination thereof.

5. The method of claim 1 wherein the *P. amylolyticus* is obtained from a *Tipula abdominalis* hindgut.

6. The method of claim 3 wherein the drying is carried out by spray drying, freeze drying, tunnel drying, vacuum drying, or Air drying.

7. A method for producing a polymyxin comprising:
providing a *Paenibacillus amylolyticus*;
incubating the *P. amylolyticus* under conditions suitable for production of polymyxin E1, polymyxin E2, or the combination thereof, to result in a mixture, wherein the incubating comprises a liquid medium;
sterilizing the mixture; and
drying the mixture.

8. The method of claim 7 wherein the *P. amylolyticus* is obtained from a *Tipula abdominalis* hindgut.

9. The method of claim 7 wherein the drying is carried out by spray drying, freeze drying, tunnel drying, vacuum drying, or air drying.

10. The method of claim 1 wherein the incubating comprises aerobic conditions.

11. The method of claim 1 wherein the incubating comprises a liquid medium.

12. The method of claim 7 wherein the incubating comprises aerobic conditions.

13. A method for producing a polymyxin comprising:
providing a *Paenibacillus amylolyticus*;
incubating the *P. amylolyticus* under conditions suitable for production of polymyxin E1, polymyxin E2, or the combination thereof; and
purifying the polymyxin E1, polymyxin E2, or the combination thereof.

14. The method of claim 13 further comprising drying the polymyxin E1, polymyxin E2, or the combination thereof.

15. The method of claim 13 wherein the *P. amylolyticus* is obtained from a *Tipula abdominalis* hindgut.

16. The method of claim 14 wherein the drying is carried out by spray drying, freeze drying, tunnel drying, vacuum drying, or air drying.

17. The method of claim 13 wherein the incubating comprises aerobic conditions.

18. The method of claim 13 wherein the incubating comprises a liquid medium.

19. A method for producing a polymyxin comprising:
providing a *Paenibacillus amylolyticus*;
incubating the *P. amylolyticus* in a liquid medium under conditions suitable for production of polymyxin E1, polymyxin E2, or the combination thereof, to result in a mixture;
sterilizing the mixture; and
drying the mixture.

20. The method of claim 19 wherein the *P. amylolyticus* is obtained from a *Tipula abdominalis* hindgut.

21. The method of claim 20 wherein the drying is carried out by spray drying, freeze drying, tunnel drying, vacuum drying, or air drying.

22. The method of claim 20 wherein the incubating comprises aerobic conditions.

* * * * *